(12) United States Patent
Taskinen et al.

(10) Patent No.: US 10,973,731 B2
(45) Date of Patent: Apr. 13, 2021

(54) PULSATION MASSAGE APPARATUS

(75) Inventors: Tapani Taskinen, Espoo (FI); Aki Backman, Althdorf (DE)

(73) Assignee: LYMPHATOUCH OY, Helsinki (FI)

( * ) Notice: Subject to any disclaimer, the term of this patent is extended or adjusted under 35 U.S.C. 154(b) by 1105 days.

(21) Appl. No.: 13/991,197

(22) PCT Filed: Nov. 30, 2011

(86) PCT No.: PCT/FI2011/051064
§ 371 (c)(1),
(2), (4) Date: Jun. 3, 2013

(87) PCT Pub. No.: WO2012/089910
PCT Pub. Date: Jul. 5, 2012

(65) Prior Publication Data
US 2013/0296744 A1    Nov. 7, 2013

(30) Foreign Application Priority Data
Dec. 1, 2010 (FI) ....................... 20106268

(51) Int. Cl.
*A61H 7/00* (2006.01)
*A61H 23/02* (2006.01)
*A61N 5/06* (2006.01)

(52) U.S. Cl.
CPC .............. *A61H 7/00* (2013.01); *A61H 7/005* (2013.01); *A61H 7/008* (2013.01);
(Continued)

(58) Field of Classification Search
CPC .......... A61H 7/00; A61H 7/001; A61H 7/002; A61H 7/003; A61H 7/004; A61H 7/005; A61H 7/007; A61H 7/008
See application file for complete search history.

(56) References Cited

U.S. PATENT DOCUMENTS

| 5,681,026 A | 10/1997 | Durand |
| 6,706,006 B2 * | 3/2004 | Kostrov ................. A61H 9/005 601/10 |

(Continued)

FOREIGN PATENT DOCUMENTS

| CN | 1130348 A | 9/1996 |
| FI | 120078 | 6/2009 |

(Continued)

OTHER PUBLICATIONS

RU Office Action, dated Oct. 2, 2015; Application No. 2013129457/14(043853).

(Continued)

*Primary Examiner* — LaToya M Louis
(74) *Attorney, Agent, or Firm* — Nixon & Vanderhye

(57) ABSTRACT

An adjustable massage apparatus, whose massage effect is based on the suction effect created in association with the treatment head, the treatment head of the apparatus including a surface which comes in contact with the skin, a frame, and in connection with this surface a low-pressure chamber and a low-pressure hose in connection with the low-pressure chamber for created low-pressure suction in order to lift the skin tissue. The apparatus is mainly characterized in that a valve is arranged in connection with the low-pressure hose for adjusting the low-pressure suction created in the low-pressure chamber so that the pressure in the low-pressure chamber is oscillating between an upper limit and a lower limit.

20 Claims, 1 Drawing Sheet

(52) U.S. Cl.
CPC .... *A61H 23/0245* (2013.01); *A61H 2007/009* (2013.01); *A61H 2201/0176* (2013.01); *A61H 2201/0207* (2013.01); *A61H 2201/10* (2013.01); *A61H 2201/5007* (2013.01); *A61H 2201/5043* (2013.01); *A61H 2201/5058* (2013.01); *A61H 2201/5064* (2013.01); *A61H 2201/5071* (2013.01); *A61H 2201/5082* (2013.01); *A61H 2201/5097* (2013.01); *A61H 2230/00* (2013.01); *A61H 2230/505* (2013.01); *A61H 2230/655* (2013.01); *A61N 5/06* (2013.01)

(56) References Cited

U.S. PATENT DOCUMENTS

| | | | |
|---|---|---|---|
| 2003/0014022 | A1 | 1/2003 | Lockwood et al. |
| 2006/0211958 | A1* | 9/2006 | Rosenberg ......... A61H 23/0236 601/9 |
| 2008/0091126 | A1* | 4/2008 | Greenburg ............ A61H 9/005 601/9 |
| 2008/0200778 | A1* | 8/2008 | Taskinen ................ A61H 7/005 600/306 |
| 2011/0098615 | A1* | 4/2011 | Whalen ............ A63B 21/00181 601/151 |

FOREIGN PATENT DOCUMENTS

| | | |
|---|---|---|
| GB | 1417989 | 12/1975 |
| JP | 2005185491 | 7/2005 |
| JP | 2008-532591 | 8/2008 |
| JP | 2009513208 | 4/2009 |
| RU | 2187294 | 8/2002 |
| WO | 0067692 | 11/2000 |
| WO | 03005921 | 1/2003 |
| WO | 2007051896 | 5/2007 |
| WO | 2007068060 | 6/2007 |
| WO | 2008063478 | 5/2008 |

OTHER PUBLICATIONS

Japan Office Action dated Jan. 20, 2016, with English Translation; Application No. 2013-541397.
Chinese Office Action, dated Aug. 29, 2014, from corresponding CN application.
International Search Report dated Apr. 16, 2012, corresponding to PCT/FI2011/051064.
Finnish Search Report dated Jul. 4, 2011, corresponding to the Foreign Priority Application No. 20106268.

* cited by examiner

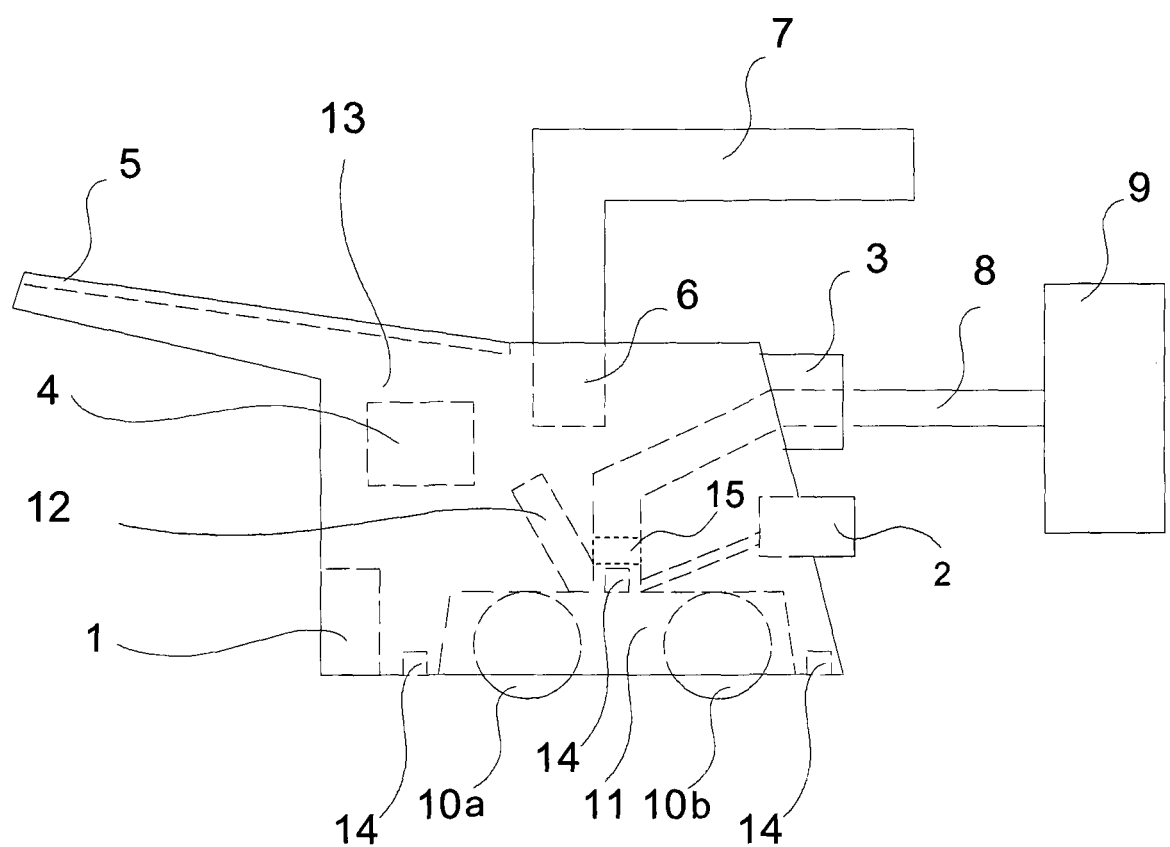

PULSATION MASSAGE APPARATUS

TECHNICAL FIELD

The object of the invention is an adjustable massage apparatus, the massage effect of which is based on variation of pressure in the low-pressure chamber of the apparatus.

PRIOR ART

Massaging affects skin and muscles in many different ways. Massage is a pressing movement applied to soft tissues for treatment purposes, and it is performed in the form of stroking, rubbing, squeezing and different types of tapping. Traditionally, massage aims at improving the metabolism of musculoskeletal system, relaxing the tension of muscles and maintaining working capacity.

Today, massage is increasingly performed using different types of devices, in which case massage is also used for such purposes as plastic and corrective treatment, rheumatic problems, burn injuries, treatment of blood circulation disorders, treatment of swelling, treatment of cellulite, stimulation of lymphatic fluids, for relaxing and firming the tissues and treatment of fibromyalgia. Subcutaneous suction-shaping massage of fat and connective tissues stimulates metabolism, blood circulation and restores firmness of tissues and removes cellulite, swelling and muscle tension. The treatment also produces positive results for fibromyalgia pains, scar tissue problems, conditions resulting from sport activities, insomnia and stress.

The method of massage depends on the treatment to be performed. Suction roller treatment is used especially for treating skin problems such as cellulite and swelling. It is performed using a device consisting of a treatment head, which is moved on top of the skin. This treatment head is connected to the suction apparatus with a flexible cord in order to create a vacuum on the skin as the treatment head moves against the patient's body. A suction roller apparatus comprises rollers, in between which there is a suction chamber which is open at the bottom, into which suction is created providing a bulge in the skin. The fold of the skin formed from the skin bulge is pressed between the rollers against roller surfaces.

Massage may be enhanced by causing oscillation to tissues. Different oscillation frequencies have different effects on body and tissues. Frequencies observed to be suitable are among others between 18 and 33 Hz.

In prior art apparatuses, oscillation of tissues is caused by a shaker plate on which the patient is standing. The shaker plates shake the skeleton, which further shakes tissues. This is stressing for the body, especially the skeleton, which in this case acts merely as a middle piece for transferring vibration, and not as a target of treatment. Moreover, prior art devices use mechanically vibrating devices against tissue. Mechanical devices require pressing of tissue, which is not beneficial for tissue fluid mobility.

The object of the invention is to improve the shortcomings of prior art devices mentioned above and to provide an apparatus for treating tissues.

DESCRIPTION OF THE INVENTION

The object of the invention is an adjustable massage apparatus, the massage effect of which is based on the suction effect created in association with the treatment head of the apparatus, the treatment head of the apparatus comprising a surface which comes in contact with the skin, a frame, and a low-pressure chamber in connection with this surface and a low-pressure hose in connection with the low-pressure chamber for created low-pressure suction in order to lift the skin tissue. The apparatus is mainly characterized in that a valve (15) is arranged in the low-pressure hose (8) for adjusting low-pressure suction created in the low-pressure chamber such that the pressure of the low-pressure chamber is oscillating between an upper limit and a lower limit.

In one embodiment, the low-pressure suction is also arranged to be adjustable based on results measured by the sensor (14).

In one embodiment, said upper limit and lower limit of pressure variation are arranged to be adjustable.

In one embodiment, the massage apparatus is arranged to provide a pressure oscillation frequency of at least 5 Hz.

In one embodiment, the massage apparatus is arranged to provide a pressure vibration frequency of at most 100 Hz.

In one embodiment, the massage apparatus is arranged to provide to the low-pressure chamber simultaneously a pulsating low-pressure treatment, which has a frequency of below 5 Hz, and an oscillation treatment, which has a frequency of more than 5 Hz. Moreover, in one embodiment a high frequency oscillation treatment is added to the suction phase of the low frequency pulsating low-pressure treatment. With high frequency may in this instance be meant for example a impulse-like pressure change or oscillation with a frequency of for example more than 5, 10 or 15 Hz.

In one embodiment, the valve is arranged to be controlled by pulse width modulation for adjusting the low-pressure in the low-pressure chamber.

In one embodiment, the low-pressure hose is arranged to be used as a pressure reservoir for accelerating pressure variations in the low-pressure chamber.

In one embodiment, the low-pressure hose is arranged to function in higher negative pressure than the low-pressure chamber for making use of pulse width modulation under control of the valve.

In one embodiment, the apparatus has a sensor for measuring specific frequency of the tissue, the measurements of which determine the adjustment. Adjustment of oscillation for the measured specific frequency of the tissue provides a powerful treatment effect even with small outputs. On the other hand, the measured specific frequency of the tissue may be avoided willfully, if the treatment is wished to be more cautious.

The preferred embodiments of the invention are presented in the subclaims.

An embodiment of the invention comprises two rollers, which are in connection with the apparatus frame, between which a negative pressure is formed in the low-pressure chamber. The rollers move against the skin surface, but they may also be static. Also, there can be one or more rollers. In other types of embodiments, the treatment head may just have a cavity at the low-pressure chamber, or sliding surfaces can be used instead of rollers.

A massage apparatus according to an embodiment comprises advantageously different sensors, one of which, for example, measures the composition of the skin tissue, such as fluid content, and advantageously also fat content, oil content, and swelling. Two sensors may be also used for measuring fluid and fat contents. The second sensor, for example, measures the raised skin (bulge) produced by the suction effect, and the third sensor measures, for example, the massage force applied to the skin. The low-pressure suction and massage force are adjusted according to the results of the measurements. Massage apparatus may also comprise a fourth sensor, which measures the skin temperature, and other sensors measuring characteristics mentioned below; the low-pressure suction and massage force are then adjusted according to the measurement results obtained by these sensors. One sensor measures either one characteristic or several characteristics. Each sensor may be connected to the apparatus through a wired or wireless connection, such as, for example, a radio frequency signal, infrared signal or the like. Thus, the sensors may be an integrated part of the apparatus or a separate part of the apparatus.

In one embodiment, the adjustment is based on mechanical characteristics and/or electrical characteristics and/or structure and/or composition of the skin. Mechanical characteristics include strength, flexibility, elasticity and resilience etc. Electrical characteristics include, for example, capacitance, impedance, resistance, reactance and inductance.

In addition, adjustment may in one embodiment be based on measurements of the flow of lymphatic fluid. Measuring techniques for the flow of lymphatic fluid are selected from known techniques.

In addition, the apparatus may in one embodiment comprise a sensor for measuring the skin's blood circulation, the measurements of which determine the adjustment. Further, adjustment may be based on measurement of transepidermal water loss and skin pH.

In one embodiment, the adjustment may also be based on the measurement of the patient's experience of cutaneous pain. Based on this, either the patient him/herself, or the therapist, or both together adjust the apparatus's running parameters. Skin characteristics, when mentioned in this text, also include the pain felt and experienced on the skin. The skin refers to all skin layers i.e. epidermis, dermis, hypodermis or subcutis. The apparatus may have a sensor which registers a signal given by the patient for increasing/decreasing the suction effect, and based on which signal the adjustment is done. The patient may thus give a signal to the sensor (for example, based on the pain experienced) and the sensor then relays to the apparatus the wish for the increase/decrease of suction efficiency.

In one embodiment, the apparatus may further comprise other energy sources for warming the skin tissue and furthermore, means for automatically adjusting these energy sources to a setpoint value based on the measurements obtained by one or more sensors.

In one embodiment, measurement techniques include measurement of different sound frequencies, such as ultrasound and infrasound, techniques based on radiofrequencies and different wave lengths of light, i.e. optical measurement such as laser and infrared measurement, bioimpedance spectroscopy, magnetic resonance spectroscopy, raman spectroscopy, nuclear magnetic resonance spectroscopy, microsensor mapping, heat camera imaging, spectrofotometric intracutaneus imagining.

In one embodiment, computer program guides the masseur in the application of force by presenting the force level visually in the treatment head and/or in the external display. Low-pressure suction is adjusted automatically using the computer program, and thus it is not necessary for the masseur to adjust the low-pressure suction adjustment during the treatment. Advantageously, when the massage force exceeds the permitted value, the program stops the apparatus.

In one embodiment, it is, by monitoring the measurements, possible for the masseur to achieve an optimal or the best massaging result without skin or tissue damages. The massage performance is nearly independent of the therapist's skills when considering the subcutaneous fluid content, fat content, skin lift, the massage force applied to the skin and the suction effect.

In one embodiment, it is also possible to install, a speed measurement in the apparatus, which will calculate the optimal treatment speed. The suction can also be located inside the suction rollers.

In one embodiment, the suction force generated from inside the rollers, and the suction sector, i.e. the adjustment of the suction area, can be determined accurately in order to create a skin lift for the fold of the skin. This enables a one-roller treatment apparatus. A multi-roller solution is also possible, which makes it possible to control the skin lift even more precisely over a wider area, which also produces suction between the rollers.

In the following section, the invention will be presented with reference to certain advantageous embodiments with the use of a FIGURE to the details of which the invention however is not limited. Different embodiments may be combined or not when applicable.

FIGURE

FIG. 1 illustrates one example of a massage apparatus according to an embodiment of the invention.

DETAILED DESCRIPTION

FIG. 1 illustrates one example of a massage apparatus according to an embodiment of the invention. The massage effect of the massage apparatus is based on the suction effect created between two rollers 10a, 10b located on the frame 13 of an apparatus according to FIG. 1.

The treatment head of the apparatus comprises a frame 13 and two rollers 10a, 10b connected to the bottom part of the frame. The bottom part of the frame 13, where also the rollers 10a, 10b are located, has a low-pressure chamber 11 for low-pressure suction, which is generated through the vacuum pipe/hose 8 using a low-pressure pump 9. Necessary adjusting valves are also mounted in the low-pressure pump 9. In addition, the low-pressure hose 8 may have a valve 15, which advantageously is positioned near the low-pressure chamber.

As the treatment head of the massage apparatus is moved against the patient's skin, most comfortably using a handle 7, the effect of the low-pressure causes a fold of skin to be pulled up between the rollers 10a, 10b, and into the low-pressure chamber 11.

A computer program automatically calculates and adjusts the level of low-pressure suction to the target value, based on the measurements obtained. The parameters of the measurements which affect the target value of the low-pressure suction, include fluid content of the skin tissue, fat content of the skin tissue, the bulge i.e. the lift of the skin tissue (the size of the fold in skin) and/or the skin temperature.

In order to obtain the measurements, the apparatus comprises a sensor 1 for measuring the fluid content of the skin tissue, a sensor 12 for measuring the lift of the skin tissue, and optionally, a temperature sensor 14 for measuring the skin temperature. Additionally, the apparatus may comprise one or more elements, which operate as energy sources for treating the tissue, such as for heating, which are based on sound, light, radio frequency or electricity, for example, it can be an infrared sensor, radio frequency sensor (RF), ultrasound sensor, laser or other element that emits monochromatic light, infrasound sensor, electric resistance or electric electrode. These elements may be wired or wireless.

The measurements are used for automatically adjusting the low-pressure suction and other energy sources to the setpoint value based on one or more results measured by the sensors. Automatic adjustment of the low-pressure suction uses, for example, a control unit 4, to which is connected a microprocessor, which is either inside or outside of the apparatus. The control unit 4 receives the setpoint value of the low-pressure suction from the computer program running in the microprocessor, which calculates the setpoint value of the low-pressure suction, based on one or more measurements. Furthermore, the control unit has a central memory. The control unit, microprocessor and central memory may be integrated into the treatment head or be separate, or they may be both integrated and separate.

The massage apparatus in FIG. 1 has two or more rollers 10a, 10b, in between which negative pressure is created in the low-pressure chamber 11. It is also possible to use one or more perforated rollers, inside of which negative pressure is created (not presented). The rollers may move against each other during the massage in order to produce a pinching effect, or they may be locked at a determined distance from one another to eliminate the pinching effect.

The computer program calculates the target value of one or more on-going treatment forces, such as massage force, based on the measurements obtained and/or on the setpoint value of the suction force. Therefore, the apparatus also comprises a sensor 6 for measuring one or more on-going treatment forces, such as the level of the massage force.

The treatment head has a display 5, which displays the massage force, and the person performing the treatment may monitor the massage force from the display 5, which shows both the target value (i.e. the setpoint value) of the massage force and the on-going massage force value, and applies the force accordingly. The program stops the apparatus, if the massage force exceeds the permitted value. Furthermore, the program may be joined to the database, which contains the patient's treatment information. The display 5 is in the control panel, which may be integrated into the treatment head, or be separate, or both.

Also the power of the energy source 14 may be controlled based on the tissue measurements. A temperature measurement sensor 14 may be integrated into the treatment head, or it may be used separately.

In one embodiment of the invention, pressure of low-pressure chamber is adjusted by controlling the valve 15 so that the pressure in the pressure chamber is oscillating as desired in order to obtain a pulsation. The valve 15 is advantageously positioned as close as possible to the pressure chamber 11, for example into the low-pressure hose 8 or into the connection point of the low-pressure hose 8 and the pressure chamber 11. By positioning the valve 15 near the low-pressure chamber, the pulsating air volume is aimed to be minimized, thus making the system more reactive.

The speed of the system may further be improved by using the low-pressure hose 8 as a low-pressure reservoir. Thus, higher or lower pressure may be achieved in the low-pressure hose compared to the pressure desired in the low-pressure chamber in a subsequent change. If, for example, a pulsation of from 150 to 200 mmHg is desired, the pressure of the low-pressure chamber is 150 mmHg and if in the subsequent phase a pressure of 200 mmHg is desired, the pressure of the low-pressure hose pressure may already be set for example to 500 mmHg, so that upon opening of the valve a pressure of 200 mmHg is achieved quickly in the low-pressure chamber and the valve may be closed. Subsequently a pressure of 150 mmHg is again desired, in which case a pressure of for example 50 mmHg may be set in the hose, so that a change from 200 mmHg to 150 mmHg is quick again. Furthermore, in one embodiment the low-pressure chamber positioned against the target may be either sealed or it may have a controlled leakage, for example, through a small opening.

The pressure of the low-pressure chamber 11 may be adjusted by using, for example under control of the valve 15, a pulse relation for adjusting the average low-pressure, when the low-pressure is higher in the low-pressure hose 8 than in the treatment head. In one embodiment, it is possible to combine slow, pulsating low-pressure to a faster impulse-like oscillation treatment, i.e. the oscillation treatment is modulated by a pulsating low-pressure treatment.

The pulsation frequency of the low-pressure chamber 11 may be for example from 2 to 200 Hz, preferably from 5 to 100 Hz. Advantageous frequency zones for the treatment are for example 18 Hz to 20 Hz for enhancing tissue fluid mobility, from 21 Hz to 25 Hz for limbering-up and warming-up, from 26 Hz to 28 Hz for enhancing mobility of joints and fascias, and from 29 Hz to 33 Hz for relieving pain.

Different characteristics of the embodiments may be combined when applicable for obtaining new embodiments.

It is evident to a person skilled in the art that the exemplary embodiments shown above are relatively simple for sake of clarity of the description, as regards their structure and functionality. It is possible to construct different and rather complex solutions by following the model presented in this patent application, which solutions take advantage of the inventive principle presented in this patent application.

The invention claimed is:

1. An adjustable massage apparatus, comprising:
a central unit comprising a low-pressure pump;
a treatment head, a massage effect being realized based on a suction effect created in association with the treatment head, the treatment head comprising a surface to be faced in contact against skin, a frame, and a low-pressure chamber including a hose connection point and being arranged in connection with the surface; and
a low-pressure hose that connects the central unit to the treatment head, the low-pressure hose having i) a first end portion with a valve and ii) a second end,
wherein the second end of the low-pressure hose is connected to the low-pressure pump, and
wherein the first end portion of the low-pressure hose is connected to the hose connection point of the low-pressure chamber with the valve located at the at the hose connection point of the low-pressure chamber so that the hose, via the valve, provides sole low-pressure flow to the treatment head;
wherein with the surface in contact against the skin, a low-pressure is provided by the low-pressure pump, via the low-pressure hose, in the low-pressure chamber for creating a low-pressure suction at the skin in order to lift tissue of the skin; and
the valve being adjustable for adjusting the low-pressure suction created in the low-pressure chamber, via the low-pressure hose, so that pressure in the low-pressure chamber is oscillating between an upper limit and a lower limit,
wherein said low-pressure hose is arranged as a pressure reservoir that accelerates pressure variations in the low-pressure chamber, and
wherein the apparatus is configured so that the low-pressure in the low-pressure hose is arranged to be higher than the upper limit or lower than the lower limit when the valve is closed for achieving the upper limit or the lower limit more quickly upon opening of the valve.

2. The massage apparatus according to claim 1, further comprising a sensor located at the hose connection of the low pressure chamber and adjacent the valve,
   wherein the valve is adjusted to adjust the low-pressure suction based on results measured by the sensor.

3. The massage apparatus according to claim 1, wherein the valve is adjusted to adjust said upper limit and said lower limit of pressure variation are arranged to be adjustable.

4. The massage apparatus according to claim 1, wherein, under control of the valve, the low-pressure chamber is subject to a pressure oscillation frequency of at least 5 Hz.

5. The massage apparatus according to claim 4, wherein, the pressure oscillation frequency is at most 100 Hz.

6. The massage apparatus according to claim 1, wherein, under control of the valve, the low-pressure chamber is subject to, simultaneously, a pulsating low-pressure treatment, which has a frequency of below 5 Hz, and an oscillation treatment, which has a frequency of more than 5 Hz.

7. The massage apparatus according to claim 6, wherein to a suction phase of said pulsating low-pressure treatment is added a further oscillation treatment, which has a frequency of more than 5 Hz.

8. The massage apparatus according to claim 1, wherein, the valve is arranged within the first end portion of the low-pressure hose at the hose connection of the low pressure chamber.

9. The massage apparatus according to claim 8, further comprising a sensor located at the hose connection of the low pressure chamber and adjacent the valve,
   wherein the valve is adjusted to adjust the low-pressure suction based on results measured by the sensor.

10. The massage apparatus according to claim 1, further comprising, at least partly in the low-pressure chamber, suction rollers, wherein negative pressure is arranged to be created between the suction rollers.

11. The massage apparatus according to claim 1, further comprising at least one sensor, wherein the at least one sensor measures at least one of skin composition and swelling, the measurements of the at least one of skin composition and swelling by the at least one sensor determining adjustment of the valve for adjusting the low-pressure suction.

12. The massage apparatus according to claim 1, further comprising at least one sensor, wherein the at least one sensor measures at least one mechanical characteristic of the skin, including at least one of the group consisting of strength, elasticity, and resilience, the measurements of the at least one mechanical characteristic by the at least one sensor determining adjustment of the valve for adjusting the low-pressure suction.

13. The massage apparatus according to claim 1, further comprising at least one sensor, wherein the at least one sensor measures at least one electrical characteristic of the skin, including at least one of the group consisting of capacitance, impedance, resistance, reactance, and inductance, the measurements of the at least one electrical characteristic by the at least one sensor determining adjustment of the valve for adjusting the low-pressure suction.

14. The massage apparatus according to claim 1, further comprising at least one sensor, wherein the at least one sensor measures flow of lymphatic fluid, the measurements of the flow of lymphatic fluid by the sensor determining adjustment of the valve for adjusting the low-pressure suction.

15. The massage apparatus according to claim 1, further comprising at least one sensor, wherein the at least one sensor measures blood circulation of the skin, the measurements of the blood circulation of the skin by the sensor determining adjustment of the valve for adjusting the low-pressure suction.

16. The massage apparatus according to claim 1, further comprising at least one sensor, wherein the at least one sensor measures transepidermal water loss, the measurements of the transepidermal water loss by the at least one sensor determining adjustment of the valve for adjusting the low-pressure suction.

17. The massage apparatus according to claim 1, further comprising at least one sensor, wherein the at least one sensor measures a bulge of the skin tissue, the measurements of the bulge of the skin tissue by the at least one sensor determining adjustment of the valve for adjusting the low-pressure suction.

18. The massage apparatus according to claim 1, further comprising at least one sensor, wherein the at least one sensor measures a specific frequency of the tissue, the measurements of the specific frequency of the tissue by the at least one sensor determining adjustment of the valve for adjusting the low-pressure suction.

19. The massage apparatus according to claim 1, further comprising at least one sensor, wherein the at least one sensor measures temperature, the temperature measurements of the at least one sensor determining adjustment of the valve for adjusting the low-pressure suction.

20. The massage apparatus according to claim 1, wherein,
   pulse width modulation is provided to control the valve, and
   the low-pressure hose is arranged to operate in higher negative pressure than the low-pressure chamber for taking advantage of the pulse width modulation provided to control of the valve.

* * * * *